US006702782B2

(12) United States Patent
Miller et al.

(10) Patent No.: US 6,702,782 B2
(45) Date of Patent: Mar. 9, 2004

(54) LARGE LUMEN BALLOON CATHETER

(75) Inventors: John Miller, Redwood City, CA (US); Martin Dieck, Cupertino, CA (US); Maria Aboytes, East Palo Alto, CA (US); Ryan Pierce, Mountain View, CA (US)

(73) Assignee: Concentric Medical, Inc., Mountain View, CA (US)

( * ) Notice: Subject to any disclaimer, the term of this patent is extended or adjusted under 35 U.S.C. 154(b) by 40 days.

(21) Appl. No.: 09/892,349

(22) Filed: Jun. 26, 2001

(65) Prior Publication Data

US 2002/0198491 A1 Dec. 26, 2002

(51) Int. Cl.⁷ .......................... A61M 29/00; F16L 11/08
(52) U.S. Cl. .............................. 604/96.01; 604/96.01; 604/97.01; 604/99.01; 604/164.01; 604/164.13; 604/523; 604/93.01; 138/111; 138/116; 138/130; 138/123; 285/222.1; 285/123.1; 285/124.1
(58) Field of Search ................... 604/96.01, 93.01, 604/97.01, 99.01, 164.1, 164.13, 523, 528; 606/191, 194; 285/123.15, 123.1, 124.1, 222.1, 136.1; 138/111–114, 116, 122, 130, 132, 123

(56) References Cited

U.S. PATENT DOCUMENTS 3,750,058 A * 7/1973 Bankert, Jr. et al. .......... 333/95

(List continued on next page.)

FOREIGN PATENT DOCUMENTS

WO    WO 96/30074 A1    10/1996

OTHER PUBLICATIONS

Dodson, M. (Apr. 2001). "Device Reverses Blood Flow, Prevents Embolism During Carotid Procedures," ArteriA Medical Science Inc. at <<http:www.medicaldata.com/mit/detail.asp?art=04120101&MITUID=203591.

NeuroV ASx', Acute Stroke Initiateives: Neuro Vasx Sub–MicroInfusion Catheter, pp. 1–3, at <<http:www.neurovasx.com/products.html.

Primary Examiner—Ira S. Lazarus
Assistant Examiner—Tu Cam Nguyen
(74) Attorney, Agent, or Firm—Townsend and Townsend and Crew LLP

(57) ABSTRACT

This is a balloon catheter having at least two lumens. One of the lumens is a large working lumen. The balloon catheter is especially useful as a guide catheter and may be used in a variety of therapeutic and diagnostic procedures. In particular, it has value in treating neurovascular embolic strokes in combination with other devices which are delivered to the stroke site through that working lumen. The remainder of the lumens typically are used to inflate and to deflate the balloon. It is highly preferable that the balloon or inflatable member be situated in a recess in the outer wall of the inventive catheter. Additionally, the distal end of the catheter past the balloon is preferably tapered. The catheter has a very low profile as compared to other catheters of the neurovascular balloon catheter genre. It may include other features such as variable stiffness along the axis of the device and anti-kinking components. The balloon is preferably compliant in nature.

When intended for use in treating embolic stroke, the catheter may be a component of a kit including a foreign body retriever. Further, amongst other procedures, the invention includes methods of temporarily blocking a vascular lumen, of removing neurovascular or peripheral emboli. Other procedures, where diagnosis or treatment is needed in a vascular space and a large working lumen is desired, are suitable procedures for the balloon catheter.

73 Claims, 8 Drawing Sheets

U.S. PATENT DOCUMENTS

| | | |
|---|---|---|
| 4,105,022 A | 8/1978 | Antoshkiw et al. |
| 4,188,954 A | 2/1980 | Patel et al. |
| 4,259,960 A | 4/1981 | Taylor |
| 4,336,798 A * | 6/1982 | Beran .................... 128/200.14 |
| 4,484,586 A * | 11/1984 | McMickle et al. .......... 128/786 |
| 4,492,089 A * | 1/1985 | Rohmer et al. ................ 62/55 |
| 4,646,719 A | 3/1987 | Neuman et al. |
| 4,886,496 A | 12/1989 | Conoscenti et al. |
| 4,917,666 A | 4/1990 | Solar et al. |
| 5,163,911 A | 11/1992 | Sirimanne et al. |
| 5,195,972 A | 3/1993 | Inoue |
| 5,253,653 A | 10/1993 | Daigle et al. |
| 5,285,744 A * | 2/1994 | Grantham et al. ............ 141/59 |
| 5,295,994 A | 3/1994 | Bonutti |
| 5,304,134 A | 4/1994 | Kraus et al. |
| 5,304,198 A | 4/1994 | Samson |
| 5,334,160 A | 8/1994 | Ellis |
| 5,364,354 A | 11/1994 | Walker et al. |
| 5,395,334 A | 3/1995 | Keith et al. |
| 5,409,004 A | 4/1995 | Sloan |
| 5,429,605 A | 7/1995 | Richling et al. |
| 5,437,637 A | 8/1995 | Lieber et al. |
| 5,484,412 A | 1/1996 | Pierpont |
| 5,499,971 A | 3/1996 | Shapland et al. |
| 5,501,668 A | 3/1996 | Kontos |
| 5,512,051 A | 4/1996 | Wang et al. |
| 5,527,292 A | 6/1996 | Adams et al. |
| 5,552,818 A | 9/1996 | Agano et al. |
| 5,571,161 A | 11/1996 | Starksen |
| 5,573,508 A * | 11/1996 | Thornton ..................... 604/96 |
| 5,606,981 A | 3/1997 | Tartacower et al. |
| 5,620,649 A | 4/1997 | Trotta |
| 5,628,754 A | 5/1997 | Shevlin et al. |
| 5,649,909 A * | 7/1997 | Cornelius .................... 606/96 |
| 5,649,941 A | 7/1997 | Lary |
| 5,653,691 A | 8/1997 | Rupp et al. |
| 5,681,336 A | 10/1997 | Clement et al. |
| 5,683,410 A | 11/1997 | Samson |
| 5,702,439 A | 12/1997 | Keith et al. |
| 5,713,854 A | 2/1998 | Inderbitzen et al. |
| 5,728,063 A | 3/1998 | Preissman et al. |
| 5,733,301 A | 3/1998 | Forman |
| 5,743,876 A * | 4/1998 | Swanson ..................... 604/96 |
| 5,752,934 A | 5/1998 | Campbell et al. |
| 5,755,690 A | 5/1998 | Saab |
| 5,759,173 A | 6/1998 | Preissman et al. |
| 5,769,817 A | 6/1998 | Burgmeier |
| 5,772,631 A | 6/1998 | Lepor |
| 5,776,099 A | 7/1998 | Tremulis |
| 5,797,877 A * | 8/1998 | Hamilton et al. ............. 604/96 |
| 5,800,522 A | 9/1998 | Campbell et al. |
| 5,817,053 A | 10/1998 | Agarwal |
| 5,823,995 A | 10/1998 | Fitzmaurice et al. |
| 5,824,173 A | 10/1998 | Fontirroche et al. |
| 5,827,201 A * | 10/1998 | Samson et al. ............. 600/585 |
| 5,827,231 A * | 10/1998 | Harada ....................... 606/194 |
| 5,833,659 A | 11/1998 | Kranys |
| 5,833,672 A | 11/1998 | Kawata et al. |
| 5,836,892 A | 11/1998 | Lorenzo |
| 5,836,912 A | 11/1998 | Kusleika |
| 5,843,051 A | 12/1998 | Adams et al. |
| 5,860,923 A | 1/1999 | Lenker et al. |
| 5,868,704 A | 2/1999 | Campbell et al. |
| 5,868,778 A | 2/1999 | Gershony et al. |
| 5,876,375 A | 3/1999 | Penny |
| 5,876,912 A | 3/1999 | Crawley et al. |
| 5,879,361 A | 3/1999 | Nash |
| 5,895,405 A | 4/1999 | Inderbitzen |
| 5,906,606 A * | 5/1999 | Chee et al. .................. 604/527 |
| 5,919,570 A | 7/1999 | Hostettler et al. |
| 5,921,957 A * | 7/1999 | Killion et al. ................. 604/96 |
| 5,925,016 A | 7/1999 | Chornenky et al. |
| 5,938,672 A | 8/1999 | Nash |
| 5,997,558 A | 12/1999 | Nash |
| 5,997,562 A | 12/1999 | Zadno-Azizi et al. |
| 6,017,323 A | 1/2000 | Chee |
| 6,027,475 A | 2/2000 | Sirhan et al. |
| 6,027,508 A | 2/2000 | Ren et al. |
| 6,027,509 A | 2/2000 | Schatz et al. |
| 6,033,381 A | 3/2000 | Kontos |
| 6,036,697 A | 3/2000 | DiCaprio |
| 6,059,751 A | 5/2000 | Ostapchenko et al. |
| 6,066,114 A * | 5/2000 | Goodin et al. ............... 604/102 |
| 6,068,623 A | 5/2000 | Zadno-Aziz et al. |
| 6,074,407 A | 6/2000 | Levine et al. |
| 6,080,170 A | 6/2000 | Nash et al. |
| 6,090,126 A | 7/2000 | Burns |
| 6,096,055 A | 8/2000 | Samson |
| 6,120,477 A | 9/2000 | Campbell et al. |
| 6,120,904 A | 9/2000 | Hostettler et al. |
| 6,122,552 A | 9/2000 | Tockman et al. |
| 6,132,824 A | 10/2000 | Hamlin |
| 6,146,370 A | 11/2000 | Barbut |
| 6,146,372 A | 11/2000 | Leschinsky et al. |
| 6,156,054 A | 12/2000 | Zadno-Azizi et al. |
| 6,159,195 A | 12/2000 | Ha et al. |
| 6,159,219 A | 12/2000 | Ren |
| 6,165,152 A | 12/2000 | Becker et al. |
| 6,165,163 A * | 12/2000 | Chien et al. ................. 604/523 |
| 6,179,788 B1 * | 1/2001 | Sullivan ...................... 600/585 |
| 6,186,181 B1 * | 2/2001 | Schippl ....................... 138/112 |
| 6,186,978 B1 * | 2/2001 | Samson et al. ........... 604/96.01 |
| 6,190,332 B1 | 2/2001 | Muni et al. |
| 6,190,354 B1 | 2/2001 | Sell et al. |
| 6,193,686 B1 | 2/2001 | Estrada |
| 6,206,852 B1 | 3/2001 | Lee |
| 6,270,477 B1 | 8/2001 | Bagaoisan et al. |
| 6,315,757 B1 | 11/2001 | Chee et al. |

* cited by examiner

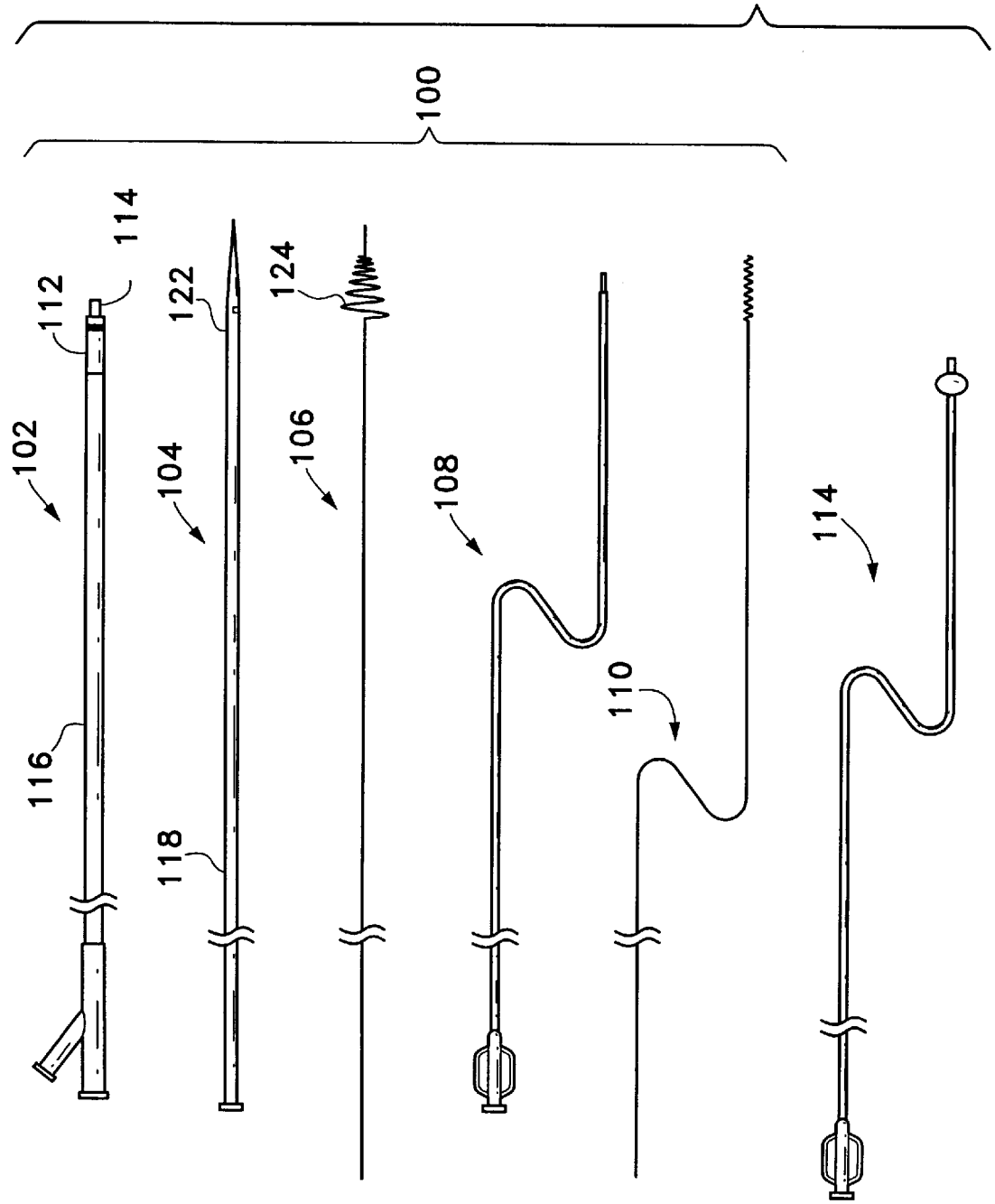

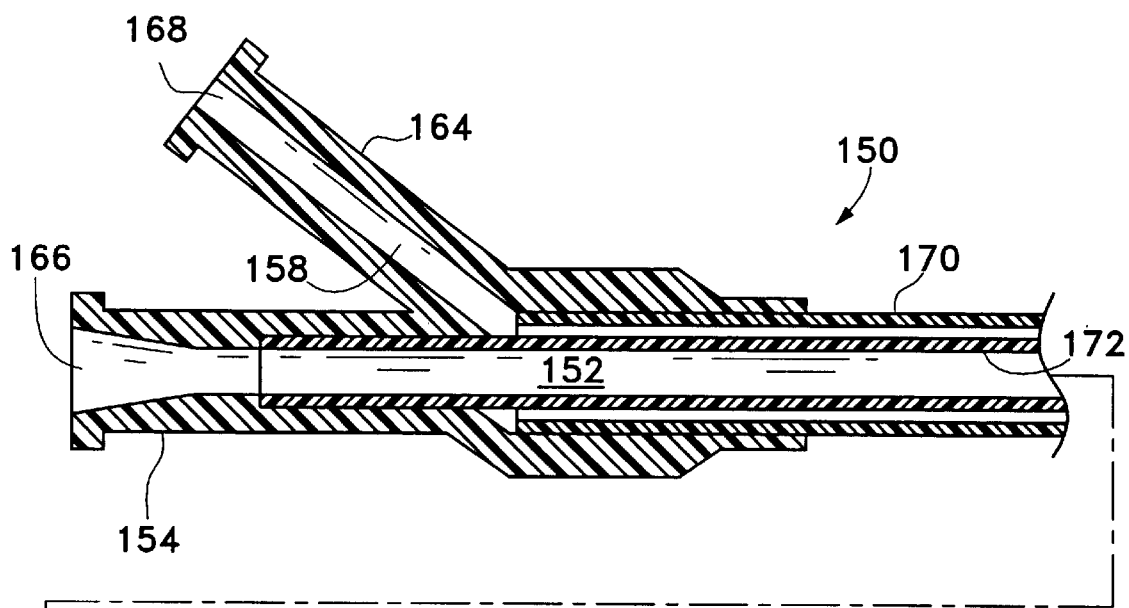
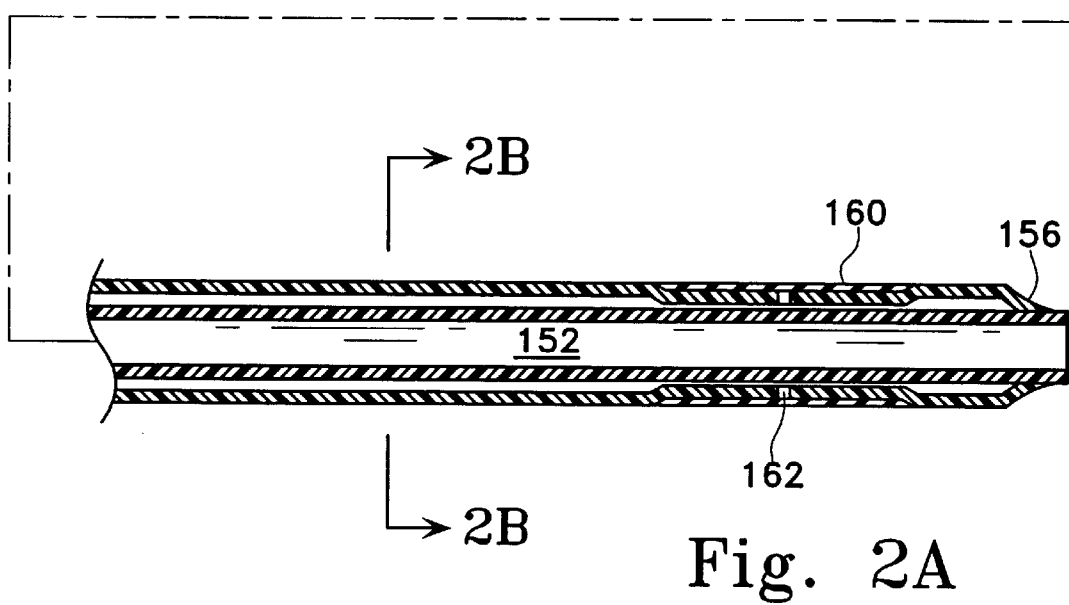
Fig. 2A
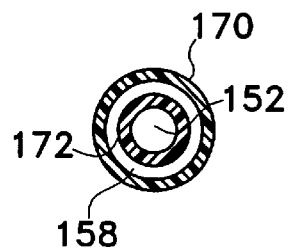
Fig. 2B

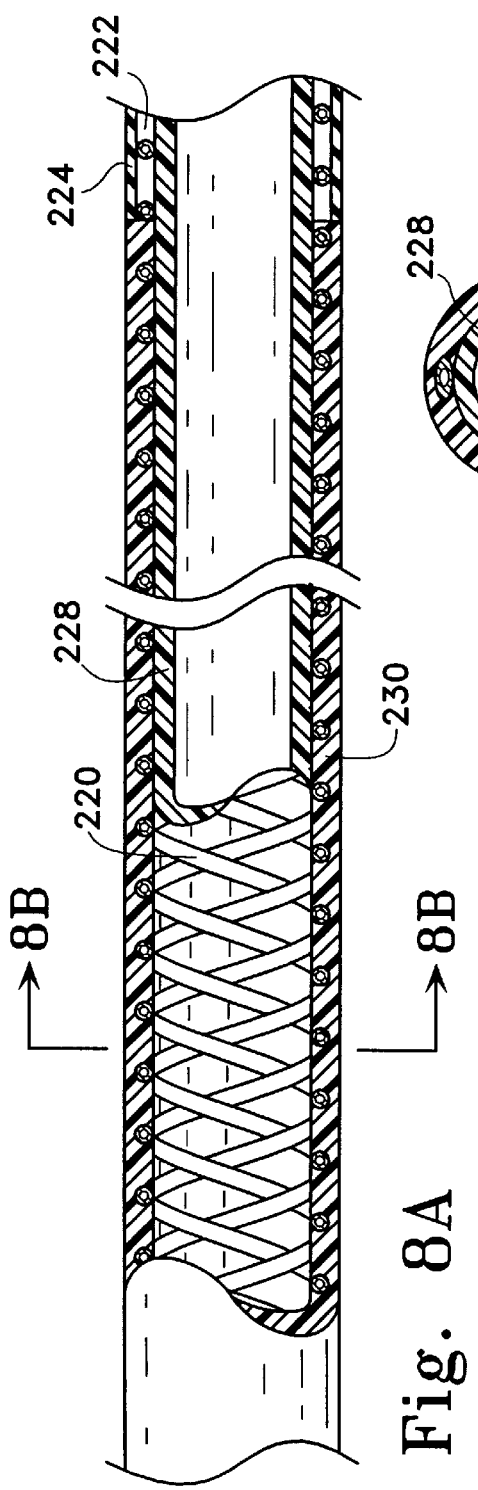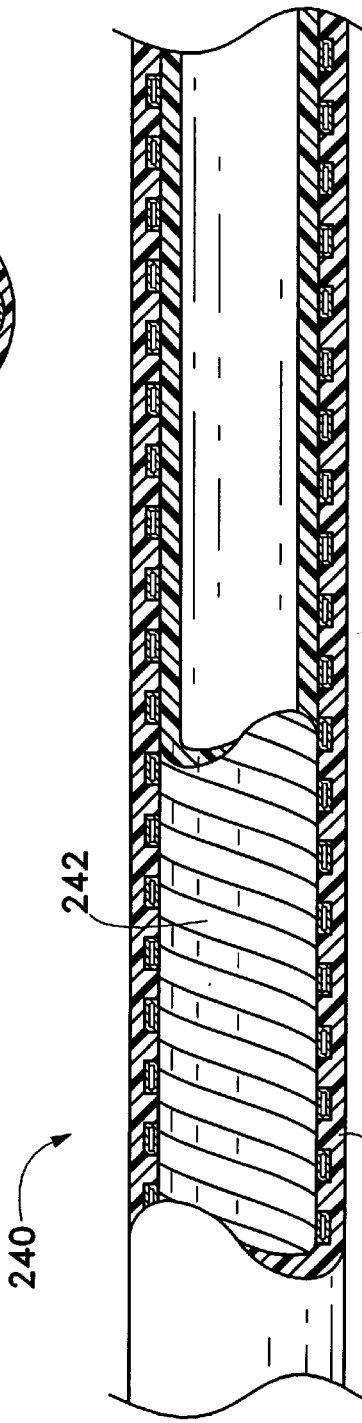

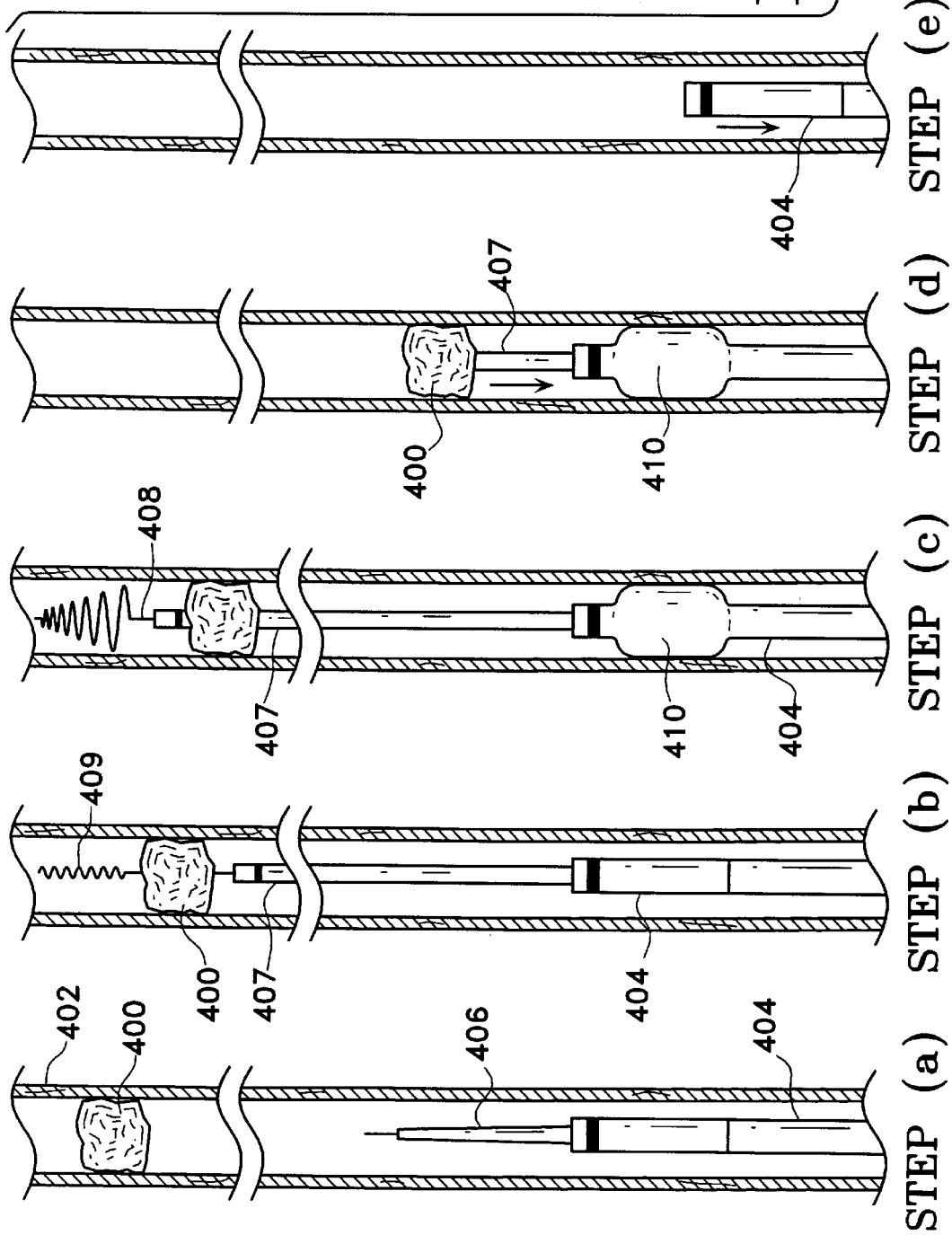

LARGE LUMEN BALLOON CATHETER

FIELD OF THE INVENTION

This invention is a medical device. In particular it is a balloon catheter having at least two lumens. One of the lumens is a large working lumen. The inventive catheter is especially useful as a guide catheter and may be used in a variety of therapeutic and diagnostic procedures variously in the neuro-, peripheral, and coronary vasculature. In particular, it has value in treating neurovascular embolic strokes in combination with other devices which are delivered to the stroke site through the working lumen. The remainder of the lumens typically are used to inflate and to deflate the balloon. It is highly preferable that the balloon or inflatable member be situated in a recess in the outer wall of the inventive catheter. Preferably, the distal end of the catheter past the balloon is tapered. The inventive device has a very low profile as compared to other catheters of the balloon catheter genre. It may include other features such as variable stiffness along the axis of the device and anti-kinking components. The balloon is preferably compliant in nature.

When intended for use in treating embolic stroke, the inventive catheter may be a component of a kit including a clot body retriever. Further, amongst other procedures, the invention includes methods of temporarily blocking a vascular lumen, of removing coronary, neurovascular, or peripheral emboli. Other procedures, where diagnosis or treatment is needed in a vascular space and a large working lumen is desired, are suitable procedures for the inventive balloon catheter.

BACKGROUND OF THE INVENTION

This invention relates generally to medical balloon catheters, their structures, and methods of using them. In particular, the present invention relates to the construction of both large and small diameter, typically braid-reinforced balloon catheters having controlled flexibility, a soft distal tip and a typically elastomeric balloon near the distal tip for the partial or total occlusion of a vessel. This catheter has a comparatively large working lumen and carries at least one inflation lumen independent of the working lumen. The inventive catheter may be used for a wide variety of medical applications, such as interventional cardiological, peripheral, or neuroradiology procedures, but is particularly useful in support of intercranial selective catheterization.

Medical catheters are used for a variety of purposes, including interventional therapy, drug delivery, diagnosis, perfusion, and the like. Catheters for each of these purposes may be introduced to target sites within a patient's body by guiding the catheter through the vascular system, and a wide variety of specific catheter designs have been proposed for different uses.

Of particular interest to the present invention are large lumen balloon catheters used in supporting procedures that, in turn, use small diameter tubular access catheters. Such procedures include diagnostic and interventional neurological techniques, such as the imaging and treatment of aneurysms, tumors, arteriovenous malformations, fistulas, and the like. Practical treatment of embolic stroke is novel.

The neurological vasculature places a number of requirements on the small catheters to be used there. The catheters should be quite fine. The blood vessels in the brain are frequently as small as several millimeters, or less, requiring that the intervening catheters have an outside diameter as small as one French (0.33 mm). In addition to small size, the brain vasculature is highly tortuous, requiring neurological catheters to be very flexible, particularly at the distal ends, to pass through the regions of tortuosity. The blood vessels of the brain are quite fragile, so it is desirable that the catheter have a soft, non-traumatic exterior to prevent injury.

Similarly, catheters used in supporting these procedures have similar requirements. Balloon catheters used in directing the smaller neurovascular catheters desirably have thin walls and are easily maneuverable. The central, or "working" lumen desirably is quite large to assist in effecting the procedures.

Although the peripheral and coronary vasculature is typically not as small nor as tortuous as is the neurovasculature, the advances in neurovascular catheter technology is quite applicable in advancing these procedures as well.

Typical of balloon guide catheters are those shown in U.S. Pat. No. 5,628,754, to Shevlin et al; U.S. Pat. No. 5,833,659, to Kranys; U.S. Pat. No. 5,836,912, to Kusleika; U.S. Pat. No. 5,681,336, to Clement et al; and U.S. Pat. Nos. 5,759,173 and 5,728,063, both to Preissman et al. None of these patents show the structure disclosed herein.

SUMMARY OF THE INVENTION

This invention involves a balloon catheter. The balloon is situated distally on the catheter body. Central to the inventive catheter is a large working lumen extending from one end of the catheter to the other. The outer surface of the balloon preferably has a substantially constant outside diameter. The balloon is situated in a recessed region at the distal end preferably just proximal of a soft, tapered tip.

A preferred variation of the inventive balloon catheter is made up of an outer or first elongate tubular member having an outer surface, a proximal end, and a distal end. This first elongate member has the noted substantially constant diameter and the radially recessed region near the distal end containing the balloon. Preferably the balloon is a longitudinally stretched inflatable member situated within the radially recessed region. The balloon, preferably but not necessarily compliant, is connected to at least one fluid supply lumen that is independent of the working lumen. When compliant, the balloon is preferably stretched longitudinally at least 10%, perhaps 15% or more, upon attachment to the first elongate tubular member.

In this preferred variation, a second (or inner) elongate tubular member that is substantially concentric with the first elongate tubular member forms an annular lumen between the two for supplying fluid to the balloon. The interior surface of the inner elongate member forms the working lumen.

The first elongate member joins the second elongate tubular member distal of the balloon.

The second elongate tubular member generally contains a stiffener member situated in its wall to provide kink resistance to the balloon catheter. The stiffener member may be a coil or a braid. The inner member may have varying stiffness between its distal and its proximal end, preferably formed of segments of polymers having different stiffnesses.

In other variations of the inventive catheter, the first elongate tubular member has a wall that contains one or more fluid supply lumens for inflating the balloon. Those fluid supply lumens may be within tubing, perhaps spirally embedded in the wall or perhaps a woven braid embedded in the wall. The tubing may be square tubing or round tubing or other convenient shape. The tubing may be polymeric or metallic. The metallic tubing is preferably a superelastic alloy.

Ancillary features, e.g., radio-opaque marker bands distal of said inflatable member and fluid fittings, are included.

The second elongate tubular member may include a lubricious, polymeric tubular inner-most tubing member.

Another subgeneric variation of the inventive catheter has the fluid supply lumens in the wall of the first tubing member. The lumens may be integral with the wall, e.g., passageways integral in or grooved into the first elongate tubular member and closed by an inner lubricious tubing.

Although the inventive balloon catheter desirably is used as a guide catheter, it may be designed with a flexibility, length, and diameter appropriate for use as a neurovascular, coronary, or peripheral microcatheter.

The outer member is preferably formed of polymeric tubing, but may also include a braid or helically wound coil of wire or ribbon.

An independent portion of the invention includes a braided tubular structure made up of a plurality of component tubular members each having longitudinal lumens, woven radially in and out to form the substantially tubular braided structure, potentially ending at one end in a plenum. The braided tubular structure may be made up of, e.g., polymeric tubing, metallic tubing (perhaps a superelastic alloy of nickel and titanium, such as nitinol). The braided tubular structure may also include at least one polymeric tubular member on its exterior. Preferred is a size and shape useful in devices suitable for introduction into a human blood vessel.

Although the inventive balloon catheters may be independently chosen for use with any number of procedures, they may also be incorporated into one or more kits tailored for a specific procedure. For instance, a kit might contain, e.g., a dilator having a lumen extending from a proximal end of the dilator to a distal end of the dilator and having a diameter closely fitting within the balloon catheter lumen; a microcatheter having a microcatheter lumen; a guidewire slideable within either the dilator lumen or the microcatheter lumen; and a clot retrieval device adapted to fit within the lumen of the balloon catheter with a retrieved clot. The microcatheter may be a balloon catheter.

Another desirable kit includes a microballoon catheter having a flexibility, length, and diameter appropriate for a neurovascular microcatheter, a guidewire slideable within the microcatheter lumen, and a clot retrieval device adapted to fit within the lumen of the balloon catheter and extend to a radially expanded state.

The catheter may be used in a variety of procedures such as removing an embolus from a vascular lumen, e.g., in sites as varied as the middle cerebral artery, the periphery, or the coronary vessels, by the steps of: introducing the balloon catheter to a position proximal said embolus, extending a microcatheter from the distal end of said balloon catheter to penetrate the embolus, extending a clot removal device through the embolus past the microcatheter, inflating the balloon of the balloon catheter to temporarily occlude the vascular lumen, withdrawing the microcatheter, the clot removal device, and the embolus into or adjacent the balloon catheter, deflating the balloon, and withdrawing the retriever and embolus into the balloon catheter. In any of these procedures, the microcatheter may be a balloon microcatheter.

Other clot removal devices may be used in combination with the inventive catheter.

The inventive catheter may be used for treating a site in a vascular lumen or performing a diagnostic step in a vascular lumen by the steps of introducing the balloon catheter to a position in the lumen, inflating the balloon of said balloon catheter to temporarily occlude the vascular lumen, treating the site or performing a diagnostic step at the site, deflating the balloon, and withdrawing the balloon catheter.

BRIEF DESCRIPTION OF THE DRAWINGS

FIG. 1 shows a kit of devices including the inventive balloon catheter (used as a guide catheter) suitable for treating embolic stroke.

FIG. 2A shows, in partial longitudinal cross section, a preferred variation of the inventive catheter. FIG. 2B shows in cross section, the variation found in FIG. 2A.

FIG. 8A shows a partial longitudinal cross section of a desirable variation using woven tubing as the inflation lumen for the balloon.

FIG. 8B shows a cross section of the catheter shaft shown in FIG. 8A.

FIG. 9 shows a further variation of a catheter shaft having one or more rectangular tubes as delivery lumen for the inflatable balloon.

FIG. 15 shows one procedure for using the inventive catheter and the allied kit for treatment of an embolism in an artery.

DESCRIPTION OF THE INVENTION

Figure 3A:
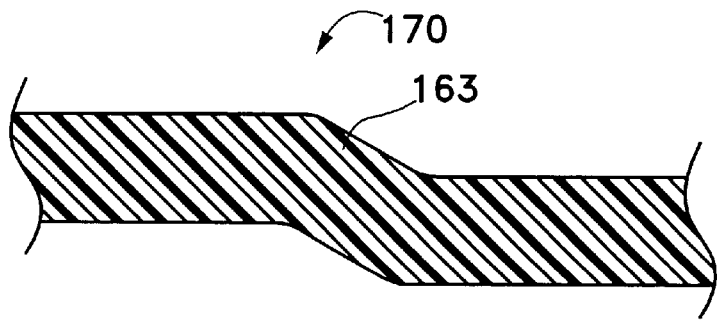
FIGS. 3A–3E show, in partial longitudinal cross-section, details of the wall construction of the outer tubular member.

The invention described here is a multi-lumen balloon catheter having a large working lumen and a distally located balloon situated in a recess in the outer surface. The device has a variety of uses depending only upon the need for a catheter having a large working lumen and the ability to block a vascular lumen for diagnosing or treating a physical malady.

FIG. 1 shows a kit (100) comprising components that likely would be used in combination to treat an embolic stroke. The kit (100) shown in FIG. 1 includes the inventive balloon catheter (102) (here used as a guide catheter), a dilator (104), a clot retrieval device (106), and an optional microcatheter (108). Optionally, the kit may include a guidewire (110) for use in guiding the microcatheter (108) to a selected site.

In overall concept, our balloon catheter (102) is a thin walled or low profile catheter having a distal inflatable member or balloon (112) and preferably a small section (113) distal of the balloon which is soft and tapered from the outside diameter of balloon (112). Desirably, the catheter shaft (116) is of a single diameter. Preferably, the balloon (112) is situated in a recess in the outer wall of the catheter shaft (116) so that the balloon (112), prior to inflation and after deflation, has the same approximate diameter as does the catheter shaft (116).

Additionally, balloon catheter (102) has at least two lumens. One lumen is a large working lumen for introduction of the other portions of the kit and whatever other devices and materials are to be introduced to the selected vascular site and one or more lumens for directing inflation fluid to balloon (112). Most preferably, the inventive balloon catheter (102) includes two lumens, the fluid supply lumen being an annular space between an inner and an outer tubular member. Other variations of the fluid supply lumen arrangement are discussed below.

Dilator (104) is a component typically having an extended shaft which fits snugly, but movably, inside the working lumen of inventive catheter (102) but is able to slide easily through that working lumen. Dilator (104) has a lumen from its proximal end (120) to its distal end (122). Distal end (122) is conical and the lumen in the middle of dilator (104) extends from the distal end (122) and is open axially. Inventive catheter (102) and dilator (104) are desirably cooperatively sized so that the conical distal region (122) of dilator (104) is extendable beyond the distal end of catheter (102).

Dilator (104) generally is for the purpose of spanning the gap between the guidewire used to direct balloon catheter (102) and the interior surface of balloon catheter (102). It provides stability to that guidewire.

One highly desirable embolus retrieval device (106) suitable for use in this kit is described in greater detail in U.S. patent application Ser. No. 09/605,143, filed Jun. 27, 2000, the entirety of which is incorporated by reference. Again, in overall concept, the clot removal device (106) is carefully tailored to engage a thrombus using the microcatheter (108) and, once the microcatheter (108) tip is downstream of the embolus, the clot retrieval device (106) is extended from encasing microcatheter (108) to allow formation of the spiral enveloping region (124) shown in FIG. 1. Desirably, balloon (112) is inflated temporarily to prevent potential for bloodflow or for a "water hammer" effect in the artery of concern. The retriever (106), with its then-included clot enveloped in a coil-like region (124), is then pulled back into the balloon catheter (102).

Other known clot retrieval devices are, of course, acceptable for inclusion in these kits.

In any event, the balloon (112) is then deflated and removed with the then-included offending emboli.

The kit may include, either as an alternative to microcatheter (108) or as an addition to the microcatheter (108), a balloon microcatheter (114) preferably of the design described herein or other suitable design. The balloon microcatheter (114) may be inflated and used in place of the microcatheter (108) to stop blood flow in that region while retrieving the thrombus.

Again, as noted elsewhere, this inventive catheter is quite valuable as a guide catheter but may be constructed in any size that meets the need of the user.

Other kits of the devices shown in FIG. 1, intended for other purposes are also contemplated, e.g., a microballoon catheter (112) made according to the invention optionally in combination with either or both of a guidewire (110) and with a thrombus retrieval device (106) is suitable for emergency stroke treatment.

Finally, the kits described here are intended to include clot retrieval devices other than the device shown in FIG. 1, although that device is preferred.

A highly preferred variation of the inventive balloon catheter (150) is shown in partial longitudinal cross section in FIG. 2A.

As noted above, the inventive device has at least two lumens. In this variation the working lumen (152) extends from the proximal end of the device (154) to the distal end of the device (156) and is open at that distal end (156). In this variation, the fluid conveyance lumen (158) is annular and connects fluidly with inflatable member or balloon (160) via a number of orifices (162).

FIG. 2B provides a cross section of the variation shown in FIG. 2A and provides a depiction of working lumen (152) and fluid flow lumen (158).

A Y-shaped fluid control and access device, e.g. a Luer-Lok (164), is shown in FIG. 2A. Fluid access device (164) has an opening (166) which accesses only working lumen (152) and further includes an opening (168) which accesses only the annular lumen (158).

Our preferred way to provide a large working lumen and one or more fluid delivery lumens is via the use of a first or outer elongate tubular member (170) concentrically surrounding a second or inner elongate tubular member (172). By placing the inner member (172) within the outer member (170), an annular fluid supply lumen (158) is created. Working lumen (152) extends axially the length of inner member (172).

Preferably, outer elongate member (170) is a polymeric tubing member having a substantially constant diameter from one end to the other with two specific exceptions. The first exception is that a region near or adjacent the distal end (156) is recessed in such a way that a balloon or inflatable member (160) may be glued or solvent welded or otherwise made to adhere to the first member (170) at the ends of the recessed region.

Returning to FIG. 2A, the distal portion of outer member (170) is desirably tapered at its most distal end (156) and joined to inner member (172).

Typically, outer member (170) is a single piece of a polymeric tubing produced from material that is used in devices of this type. Materials of construction are desirably polyurethane (e.g., Pellaflex and Pellathane), polyether-polyamide block copolymers (e.g., Pebax), polyethylene (e.g., HDPE, LDPE, and LLDPE), and others, preferably having significant flexibility.

Figure 3B:
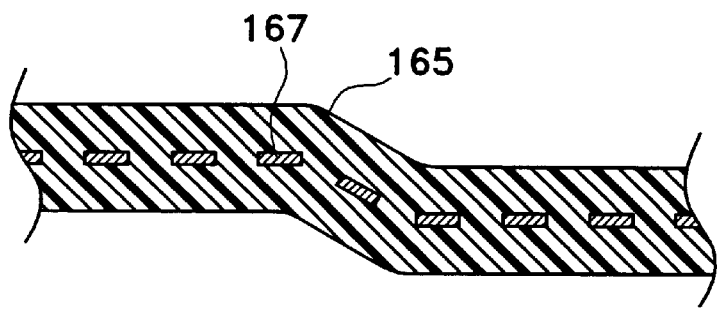
Figure 3C:
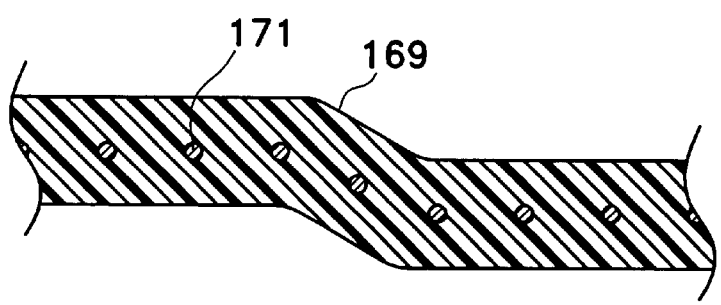
Figure 3D:
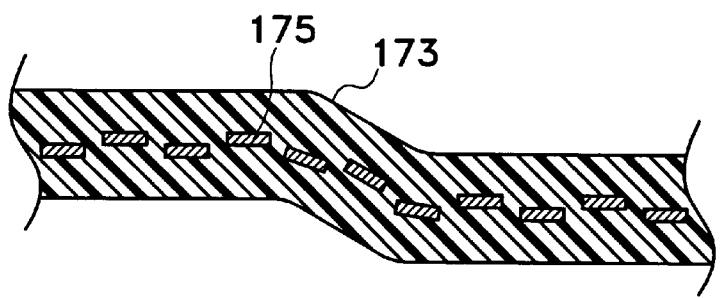
Figure 3E:
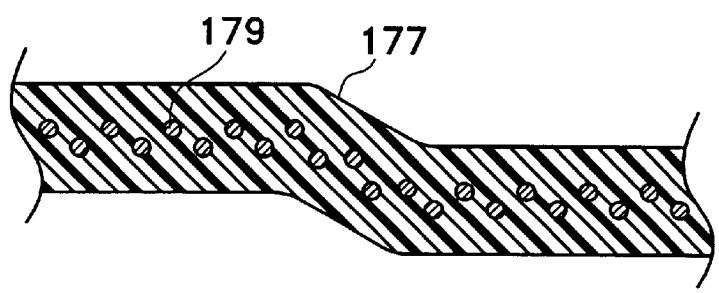

As shown in partial longitudinal cross-section in FIG. 3A, although the preferred make-up of the outer elongate member (170) is a neat polymer tubing (163) for a variety of reasons expressed elsewhere, other wall compositions are acceptable and may even be desirable for some usages. FIG. 3B shows, in partial longitudinal cross-section, an outer elongate member wall (165) containing a helically placed ribbon coil (167). FIG. 3C shows, in partial longitudinal cross-section, an outer elongate member wall (169) containing a helically placed wire coil (171). FIG. 3D shows, in partial longitudinal cross-section, an outer elongate member wall (173) containing a woven ribbon braid (175). Finally, FIG. 3E shows, in partial longitudinal cross-section, an outer elongate member wall (177) containing a woven wire braid (179). Any of the ribbon and wire discussed here may be variously metallic (e.g., stainless steels or superelastic alloys such as nitinol) or polymeric. The polymers may be single phase, e.g., such as monofilament line, or multiple strands bundled or woven together. These components may be made of a mixture of materials, e.g., super-elastic alloy and stainless steel components or of liquid crystal polymers (LCP's). Preferred because of cost, strength, and ready availability are stainless steels (SS304, SS306, SS308, SS316, SS318, etc.) and tungsten alloys. In certain applications, particularly in smaller diameter devices, more malleable metals and alloys, e.g., gold, platinum, palladium, rhodium, etc. may be used. A platinum alloy with a few percent of tungsten or iridium is sometimes used because of its high radio-opacity.

When using a super-elastic alloy in any of the component tubing members, an additional step may be desirable to preserve the shape of the stiffening braid or coil. For instance, after a braid has been woven using, e.g., 4, 8, 12, or 16 members, some heat treatment may be desirable. Braids which are not treated this way may unravel during subsequent handling or may undertake changes in diameter or spacing during that handling. In any event, the braids are placed on a heat-resistant mandrel, perhaps by weaving them onto that mandrel, and placed in an oven at a temperature of, e.g., 650° to 750° F. for a few minutes. This treatment may anneal the material in the constituent ribbon or wire but in any event provides it with a predictable shape for subsequent assembly steps. After heat-treatment, the braid does retain its shape and most importantly the alloy should retain its super-elastic properties.

Figure 4A:
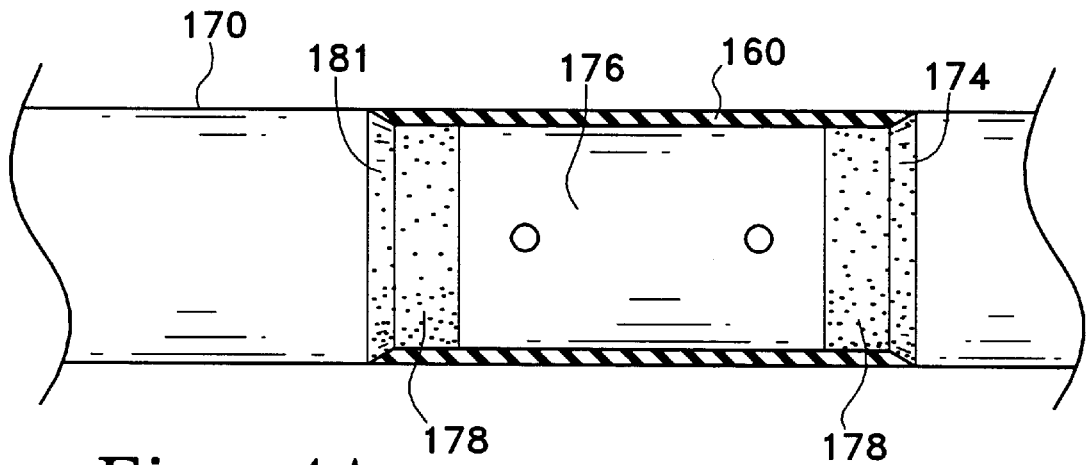
FIGS. 4A and 4B show, in partial longitudinal cross section, details of the inflatable member construction.
Figure 4B:
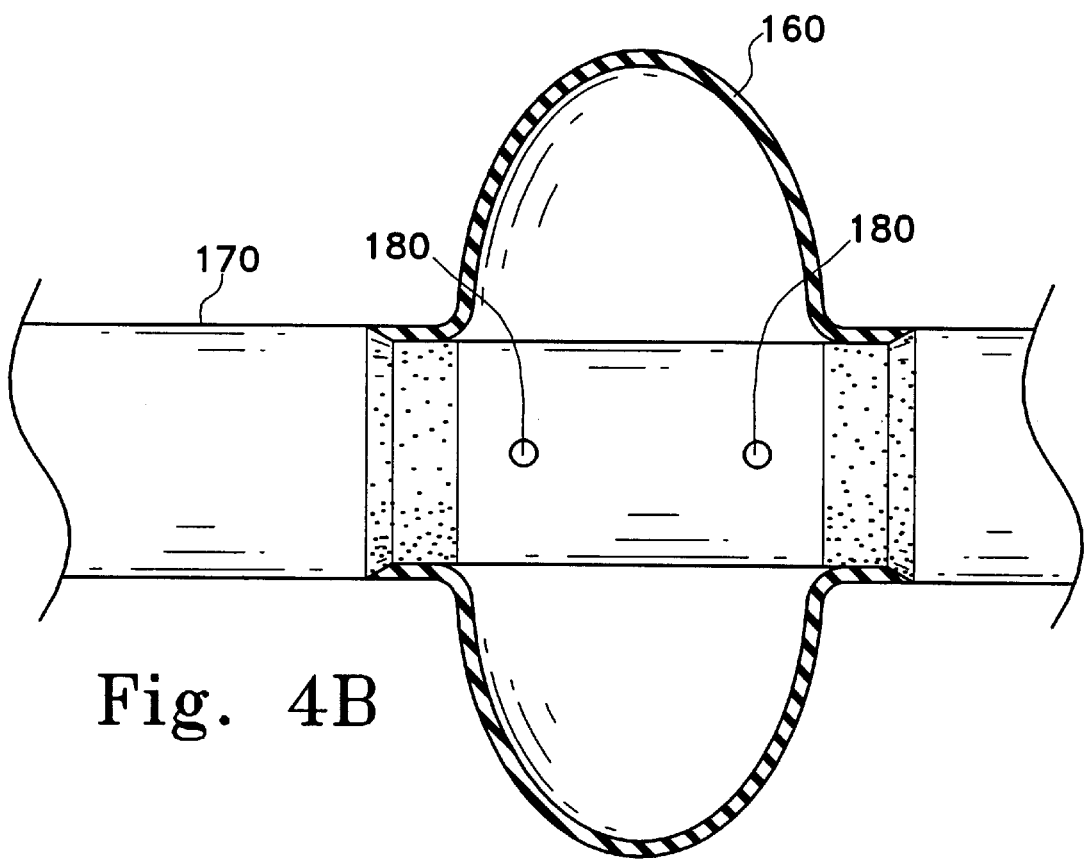

FIGS. 4A and 4B show the mounting of the balloon in a radial depression in greater detail. In FIG. 4A, two shoulders (181) and (174) may be seen rimming the depressed or recessed region (176). Also shown in the partial cutaway views found in FIGS. 4A and 4B are two regions (178) in which the recessed area (176) is etched or roughened so to permit better adhesion of the balloon material. Balloon (160), again, is only adherent to the recessed region (176) at roughened regions (178). FIG. 4B shows balloon (160) in an inflated state after a fluid passes through orifices (180) into inflatable member (160). To reiterate, deflated balloon (160), as seen in FIG. 4A, has the same approximate diameter as does substantially all of the rest of outer member (170). The orifices may be of any convenient shape, e.g., oval, square, etc. Indeed, they may be spiral cuts or the like.

Figure 5:
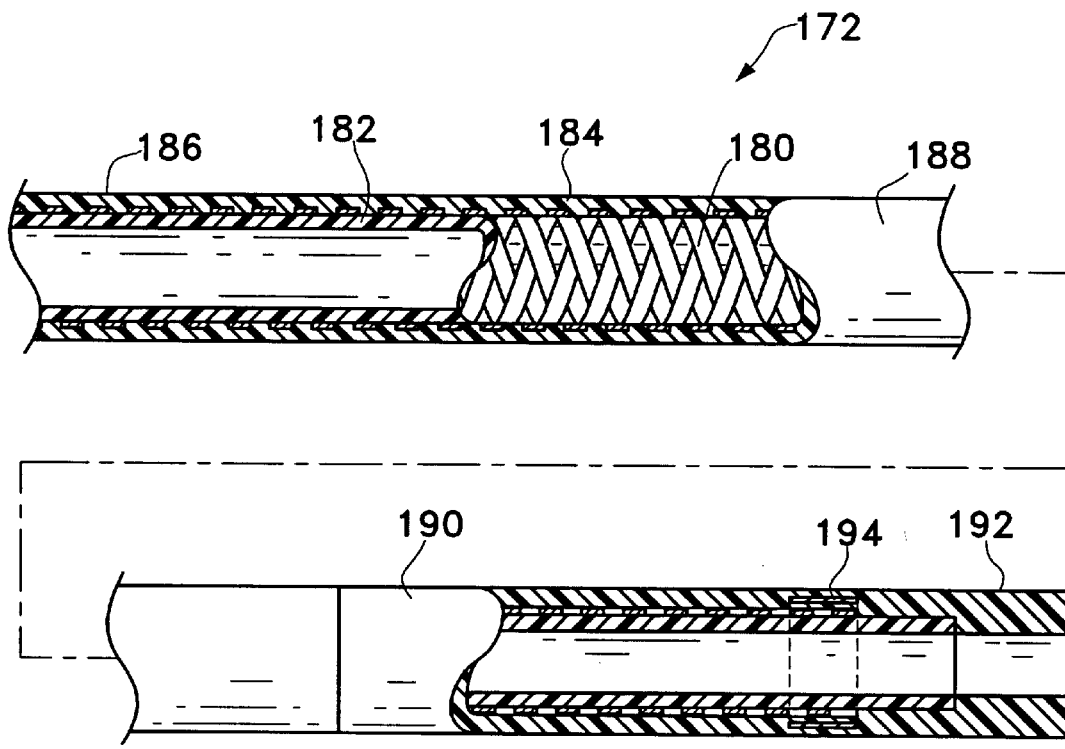
FIGS. 5, 6, and 7 show variations of the interior tubular member.
Figure 6:
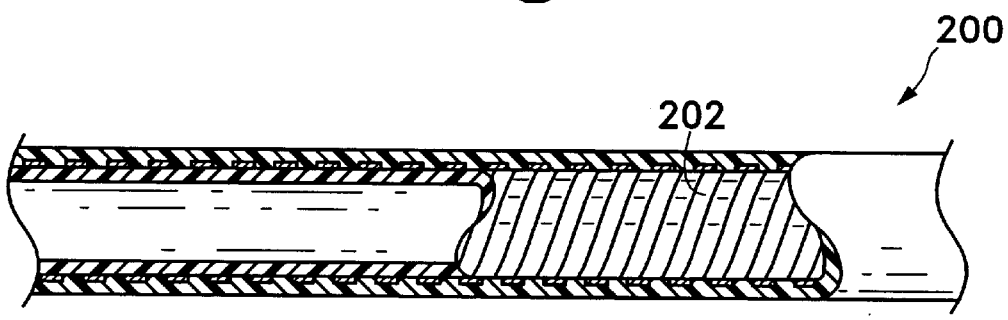
Figure 7:
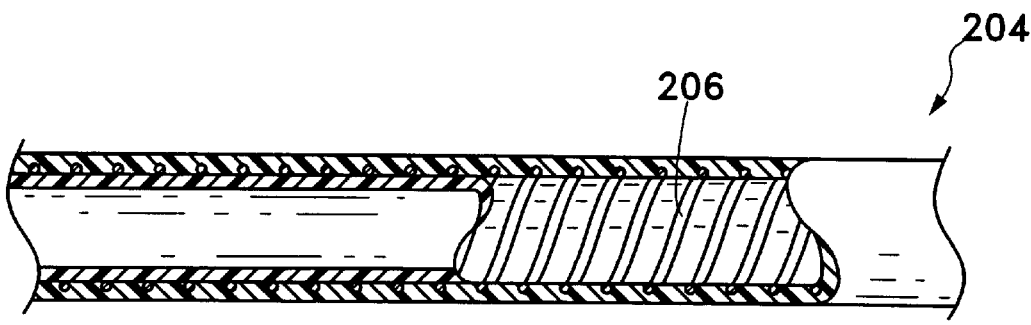

FIGS. 5, 6, and 7 show variations of the component found in FIGS. 2A and 2B as the inner elongate member (172). Inner elongate member (172), in this variation of the invention, desirably provides two important functions to the inventive catheter. Those functions are kink resistance and increasing flexibility towards the distal end of the inventive catheter. Although in other variations of the invention, such functions may be provided by the outer member, provision of these functions in the inner member allows significant economy in profile and allows for significantly greater overall flexibility and consequent ease of access to distant neurovascular locations.

FIG. 5 shows a highly preferred variation comprising a braid (180), an inner liner (182) and an outer covering (184). The braid (180) is formed from ribbons of stainless steel, superelastic alloys such as nitinol, or polymeric constructs. Although the braid may alternatively be formed from a round or oval profiled wire, a ribbon is preferred because of the overall lower profile attainable for an enhanced amount of kink resistance. For this variation, stainless steel ribbon braid is preferred. The ribbon making up the braid is preferably less than 1.5 mil in thickness, more preferably 0.7 mils to 1.5 mils, most preferably about 1 mil. The width desirably is 2.5 mils to 7.5 mils in width, more preferably about 5 mils. By "braid" here, we mean that the braid components are woven radially in and out as they progress axially down the braid structure. This is to contrast with the use of the term "braid" with co-woven coils merely laid one on top of the other in differing "handed-ness."

Inner liner (182) desirably is a very thin, e.g., 0.25 mil to 1.5 mil wall thickness, of a hard or lubricious material such as a polyfluorocarbon. Such lubricious polymers include polytetrafluoroethylene (PTFE or TFE), ethylene-chlorofluoroethylene (ECTFE), fluorinated ethylene propylene (FEP), polychlorotrifluoroethylene (PCTFE), polyvinylfluoride (PVF) or polyvinylidenefluoride (PVDF) especially preferred is PTFE. Other materials such as polyethylene (particularly HDPE), polypropylene, and polyamides (the Nylons) their mixtures and co-polymers are also acceptable.

The outer covering (184) is preferably of a significantly softer material than is that making up the inner liner (182). Moreover, it is desirable that the material making up the outer covering (184) be thermoplastic so to melt into the braid (180) or other stiffening or anti-kinking member. Materials include polyethylene (LDPE and LLDPE), polyvinylchloride (PVC), ethylvinylacetate (EVA), polyethylene terephthalate (PET), and their mixtures and copolymers. Also suitable are thermoplastic elastomers, particularly polyesters. Typical of this class is HYTREL. Polyurethanes such as Pellethane are suitable. Another copolymer of polyurethane and polycarbonate sold as Carbothane also works well. Especially desirable, though, is a block copolymer of polyethers and polyamide commercially known as PEBAX.

Additionally, the stiffness of the inner elongate member (172) may be varied by choosing polymers of different stiffness as measured by Shore Durometer values. In the preferred variation shown in FIG. 5, the outer covering (184) is made up of four distinct polymer sections. The most proximal portion (186) desirably has a Shore Durometer hardness of 65 to 78 D, preferably about 72 D. The next more distal portion (188) preferably is made up of a polymer having a Shore Durometer hardness of 50 to 60 D, preferably about 55 D. The next more distal portion (190) preferably has a Shore Durometer hardness of 35 to 45 D, preferably about 40 D. The most distal section (192) preferably has the softest Shore Durometer hardness, between 30 and 40 D, preferably about 35 D. Again, these are preferred in keeping with the preferred use in the neurovasculature. However, other uses would allow other stiffnesses.

In the preferred embodiment shown in FIG. 5, proximal section (186) has a length of about 85 to 115 centimeters, preferably about 95 to 105 centimeters, and most preferably about 100 centimeters. The next more distal section (188) preferably has a length of about 20 to 40 millimeters, more preferably about 25 to 35 millimeters and most preferably about 30 millimeters. The next more distal section (190) preferably has a length of about 50 to 60 millimeters, more preferably about 45 to 55 millimeters, and most preferably about 50 millimeters. Finally, the most distal portion preferably is quite short at about 1 to 10 millimeters., preferably about 3 to 6 millimeters., and most preferably about 4 millimeters. The lengths of these sections may be varied once this disclosure is appreciated by those having ordinary skill in this art.

The braid in this preferred variation terminates beneath a radio-opaque marker (194) located fairly distally on inner elongate member (172). Generally, the radio-opaque marker is a band or helically wound coil of a radio-opaque material such as platinum or a platinum-iridium alloy. It may be of other materials as desired or as appropriate. If the radio-opaque marker (194) is a metallic band, it is often assembled over a thin layer of PET to help with the adherence of the radio-opaque marker to the end of the braid (180).

Typically, the inner member (172) is assembled in the following fashion. A mandrel, having an appropriate size, is selected. The inner lubricious liner (182) is then slid onto that mandrel. As noted above, preferably the inner layer (182) is comprised of a material such as polyimide, polyamides such as the Nylons, high density polyethylene (HDPE), polypropylene, polyvinylchloride, various fluoropolymers (for instance, PTFE, FEP, vinylidene fluoride, their mixtures, alloys, copolymers, block copolymers, etc.), polysulfones or the like. The braid (180) is then slid onto inner liner (182), and then various outer sections of thermoplastic (186, 188, 190), the appropriately placed radio-opaque marker (194), and the distal-most portion (192) are then placed on the partially-assembled mandrel. Finally, a shrink-wrap material such as cross-linked polyethylene or a fluorocarbon (e.g., PTFE or FEP) is then placed on the outside of the assembled inner tubular member. The thus-assembled components are then subject to heat treatment at a temperature which is intended to have the effect both of shrinking the heat-shrinkable outer layer material and allowing the outer thermoplastic layers to pass their $T_g$ (glass point) and to flow into the kink resisting member, e.g., the braid (180).

Once that is accomplished, the heat-shrinkable tubing is then stripped from the assembly and the second or inner elongate tubular member (172) is ready for joining to the outer or first elongate tubular member (170) discussed above.

Additionally, the various outer sections may be dip-coated onto the inner sections using molten polymers.

FIG. 6 shows a variation (200) of the inner member which is similar in most aspects to the component (172) discussed with relation to FIG. 4 above. The difference here is the presence of helically wound coil (202) in the place of the braid (180) in FIG. 4. Similarly, FIG. 7 shows still another variation (204) of the component utilizing a helically wound wire (206) instead of the braid (180) found in FIG. 5.

Another variation of the inventive balloon catheter is a subgeneric category in which the functions of the inner longitudinal member and the outer longitudinal member spoken of in the variations above are merged into a single wall. That is to say that the annular fluid supply lumen (158) is not present in these variations and the fluid supply lumens may be those found in multiple fluid supply tubing components or extruded into the wall of the elongate lumen tubular member. In general, there is no second elongate tubular member in this set of variations.

FIGS. 8A, 8B, and 9 show variations of the invention in which the tubing which serves as the kink resistant member further serves as its fluid supply conduit.

FIGS. 8A and 8B show, respectively, a partial longitudinal cross-section and a full radial cross-section. Also seen is the placement of braided tubing terminating in a small plenum (222) just beneath the inflatable member diaphragm (224). The fluid used to inflate the balloon (224) passes through each of these tubing members (220) and conversely to deflate inflatable member (224) along the same path.

A plenum may be found at the either the distal or the proximal end of the catheter for distribution of fluid to the multiple braided tubing members. As was the case above, this variation of the first elongate tubular member may include a lubricious inner member (228) or not. Similarly, the materials making up the outer layer (230) may be of the materials discussed above. The benefit of this particular design is that it eliminates many layers of parts and yet is able to maintain the inner lumen at a maximum size.

Similarly, FIG. 9 shows another variation (240) of catheter walls suitable for use in the inventive balloon catheter. In this variation, at least one or more rectangular tubing members (242), having open inner lumen, is helically placed within the catheter section wall (244) to permit fluid flow to the inflatable balloon.

The shape of the hollow tubing found in FIGS. 8A, 8B, and 9 is not limited to those seen in the drawings. Any convenient shape, e.g., round, square, rectangular, oval, etc., will suffice.

Figure 10:
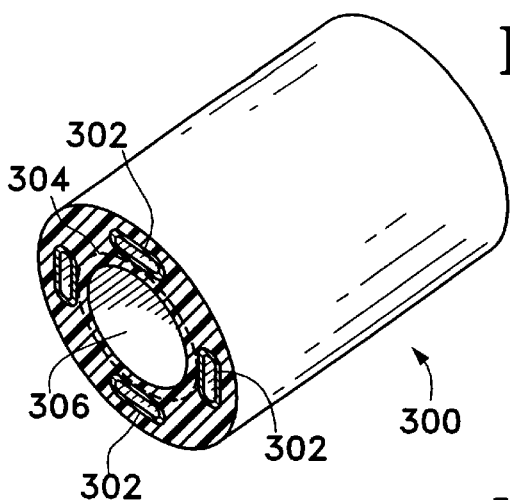
FIGS. 10, 11, 12, 13, and 14 show integrated variations of catheter shafts suitable for use in the inventive balloon catheter assembly.

FIG. 10 shows a perspective cut-away of catheter section (300), having a plurality of passageways (302) which are used as fluid passage lumen. Kink resisting member (304), e.g., a coil, braid, multiple coils, or the like, is also shown there. A working lumen (306) is also depicted. As was the case above, the catheter section (300) may be made up of a combination having an interior lubricious tubing, or may be made from a single material.

Figure 11:
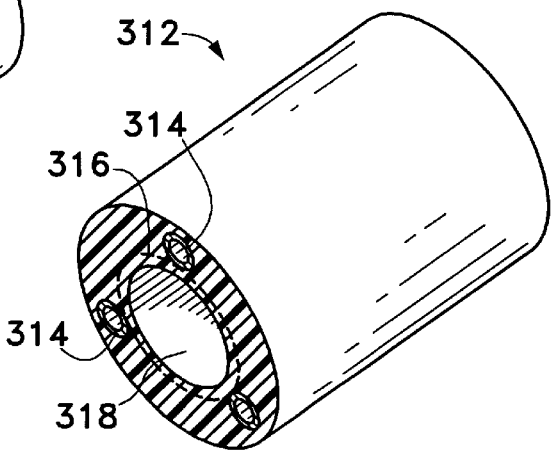

FIG. 11 shows another variation of the catheter wall section (312) useful in the inventive balloon catheter. Catheter section (312) is shown in FIG. 11 to have multiple discrete tubing members (314), which have been made integral with the wall of catheter section (312). Again, the stiffening or anti-kinking member (316) is shown to be situated exterior of the working lumen (318).

Figure 12:
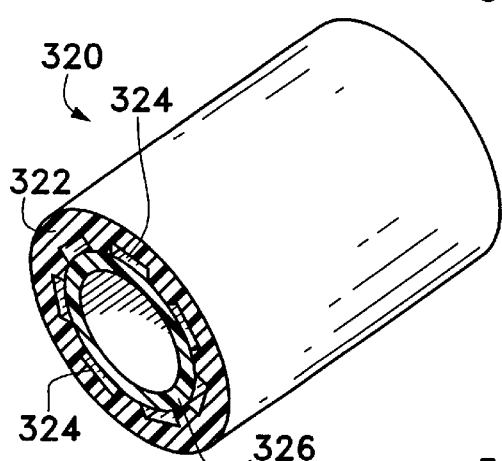

FIG. 12 shows still another variation (320) of the catheter section. In this instance, the wall is assembled by the joinder of two members. The outer member (322), typically made by extrusion, has a number of longitudinal grooves (324) placed in the outer member (322) as it is made. An inner member (326) is thereafter inserted into outer member (322) to close grooves (324) and allow them to function as fluid flow lumens to the inflatable balloon discussed above.

Figure 13:
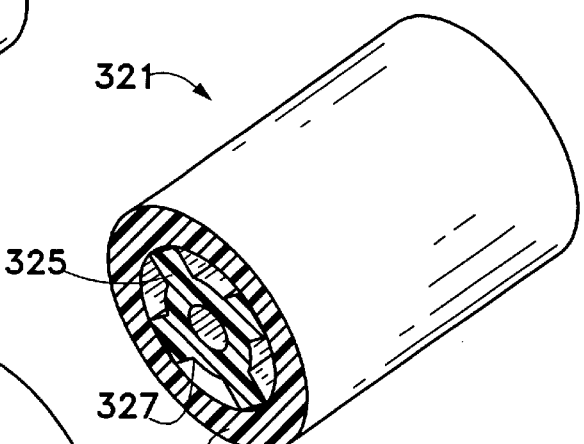

FIG. 13 shows a variation (321) of the catheter section shown in FIG. 12. Again, this wall is assembled in by joinder of two members. The outer member (323), is a simple smooth tubing. The inner member (325), an extrusion, has an number of longitudinal grooves (327). The inner member (325) is inserted into outer member (323) to close or to envelop grooves (327) and allow them to function as fluid flow lumens to the inflatable balloon discussed above.

Figure 14:
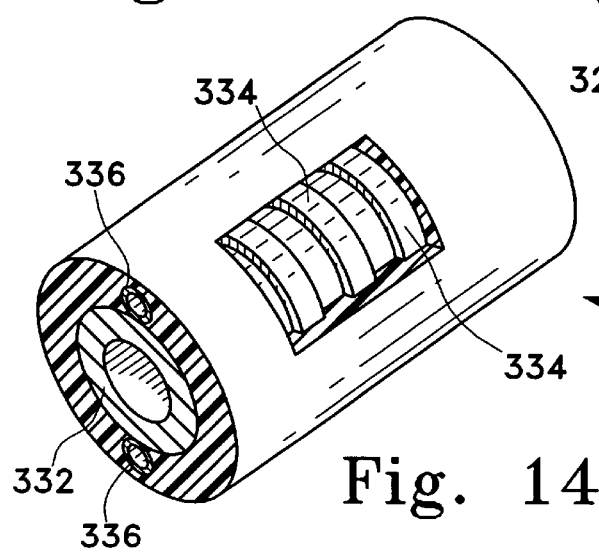

FIG. 14 shows another variation (330) of the catheter wall suitable for use in the inventive balloon catheter. In this variation, a metallic tube (332) (e.g., a "hypotube") which has been machined or otherwise cut away to form interlocking teeth in one or more places around the circumference of the tube is embedded into the catheter wall section thereby allowing the tube to bend with ease. FIG. 14 shows a pair of tubing members (336) which each have interior lumens suitable for providing fluid to the inflatable balloon.

FIG. 15 shows a five-step method for deploying the inventive balloon catheter in an artery for removal of an embolism (400) from that artery (402).

In Step (a), the inventive balloon catheter (404) with dilator (406) has been placed in the occluded vessel. In Step (b), dilator (406) has been withdrawn from balloon catheter (404) and replaced with microcatheter (407) and guidewire (409). The microcatheter (407) tip is seen approaching clot (400) and the guidewire (409) has penetrated the embolus (400) and may be seen protruding from the distal side of that clot.

In Step (c), the guidewire (409) has been replaced by retrieval member (408). Retrieval member (408) has been placed distal of clot (400) and balloon (410) on inventive balloon catheter (404) has been inflated to block the flow of blood towards embolus (400). The distal end of microcatheter (407) has been urged through the clot (400) and is distal of the clot (400). Inflation of balloon (410) has several effects. First of all, it prevents blood from carrying small portions of the embolus distally for ultimate lodging in other arterial vessels. Secondly, it quells the "water-hammer" effect which may tend to break up such clots. Thirdly, when used in the brain to remove clots in the middle cerebral artery because of the unique nature of the vasculature in that portion of the brain, closing the middle cerebral artery at this point causes backflow, which may tend to push the clot (400) back towards the open lumen of catheter (404).

Step (d) shows the removal of clot (400) and the retraction of the microcatheter (407) and embolism retriever (408) into the end of balloon catheter (404).

Finally, Step (e) shows the removal of balloon catheter (404) after the clot and the retrieval device have been withdrawn into the open end of catheter (404) and balloon (410) deflated.

The specific example described in conjunction with FIG. 15 is for the purpose of showing the practical utility of the inventive balloon catheter. The balloon catheter may be used in other processes. Other styles of embolus removing devices may be used in conjunction with the inventive balloon catheter, e.g., circular, proximal, or aspirating.

Of course, it should be apparent that this device and its clot removal ability may be used in other parts of the human body, e.g., in the periphery, the coronary, and the like. In addition, the balloon catheter may be used temporarily to occlude an artery for other diagnostic or therapeutic purposes, e.g., occluding an artery using vaso-occlusive devices or blocking bloodflow while introducing a medicine to a limited region of the vasculature.

The invention has been described and specific examples of the invention have been portrayed. The use of those specifics is not intended to limit the invention in any way. Additionally, to the extent that there are variations of the invention that are within the spirit of the disclosure and yet are equivalent to the inventions found in the claims, it is our intent that this patent cover those variations as well.

We claim as our invention:

1. A balloon catheter comprising:
   a first elongate tubular member having an outer surface, a proximal end, a distal end, having a substantial constant diameter, a working lumen extending between said distal and proximal ends and being open at said distal end, and a radially recessed region near the distal end, and
   a longitudinally stretched inflatable member situated within said radially recessed region providing said substantially constant diameter and being fluid-connectable with at least one fluid supply lumen independent of said working lumen.

2. The balloon catheter of claim 1, further comprising a second elongate tubular member substantially concentric with the first elongate tubular member and having a lumen forming the working lumen and an outer surface forming an annular space between the first elongate tubular member, said annular space being the fluid supply lumen.

3. The balloon catheter of claim 2, wherein said second elongate tubular member comprises a wall, a distal end, and a proximal end, and further comprising a stiffener member situated to provide kink resistance to the balloon catheter.

4. The balloon catheter of claim 3, wherein the stiffener member comprises a coil.

5. The balloon catheter of claim 3, where the stiffener member comprises a braid.

6. The balloon catheter of claim 2, where the second elongate tubular member has varying stiffness between said distal and said proximal end.

7. The balloon catheter of claim 6 comprising segments of polymers of different stiffness.

8. The balloon catheter of claim 1 where the inflatable member is compliant.

9. The balloon catheter of claim 1 where the inflatable member is stretched longitudinally at least 10% upon attachment to the first elongate tubular member.

10. The balloon catheter of claim 9 wherein the inflatable member is stretched longitudinally about 15% upon attachment to the first elongate tubular member.

11. The balloon catheter of claim 1 where the first elongate tubular member comprises a wall containing one or more fluid supply lumens for said inflatable member.

12. The balloon catheter of claim 11 wherein said wall comprises tubing forming fluid supply lumens.

13. The balloon catheter of claim 12 wherein the wall comprises tubing spirally embedded in said wall.

14. The balloon catheter of claim 13 wherein the wall comprises square tubing spirally embedded in said wall.

15. The balloon catheter of claim 13 wherein the wall comprises round tubing spirally embedded in said wall.

16. The balloon catheter of claim 13 where said tubing comprises polymeric tubing.

17. The balloon catheter of claim 13 where the tubing comprises metallic tubing.

18. The balloon catheter of claim 17 where said metallic tubing comprises a superelastic alloy.

19. The balloon catheter of claim 12 wherein said fluid supply lumen is comprised of a braid of square or round tubing embedded in said wall.

20. The balloon catheter of claim 19 where the braid comprises square tubing.

21. The balloon catheter of claim 19 where the braid comprises round tubing.

22. The balloon catheter of claim 19 wherein said braid comprises polymeric tubing.

23. The balloon catheter of claim 19 where the braid comprises metallic tubing.

24. The balloon catheter of claim 23 where the metallic tubing comprises a superelastic alloy.

25. The balloon catheter of claim 2 where the second elongate member further comprises a radio-opaque marker band distal of said inflatable member.

26. The balloon catheter of claim 2 wherein said first elongate tubular member is tapered distal of said inflatable member and joined to said second elongate tubular member.

27. The balloon catheter of claim 2 wherein said second elongate tubular member further comprises a lubricious polymeric tubular inner-most tubing member.

28. The balloon catheter of claim 1 wherein said at least one fluid supply lumens is integral within said first member wall.

29. The balloon catheter of claim 28 wherein said at least one fluid supply lumens comprise passageways integral in and grooved in said first elongate tubular member and further comprising a lubricious inner member tubing closing said grooved passageways radially.

30. The balloon catheter of claim 1 wherein said catheter is of a flexibility, length, and diameter appropriate for a neurovascular microcatheter.

31. The balloon catheter of claim 1 wherein said catheter is of a flexibility, length, and diameter appropriate for a guide catheter.

32. The balloon catheter of claim 1 wherein said first elongate tubular member comprises a polymeric tubing.

33. The balloon catheter of claim 1 wherein said first elongate tubular member comprises a composite wall containing a helically wound coil.

34. The balloon catheter of claim 33 wherein said helically wound coil is wound from wire.

35. The balloon catheter of claim 33 wherein said helically wound coil is wound from ribbon.

36. The balloon catheter of claim 1 wherein said first elongate tubular member comprises a composite wall containing a braid.

37. A kit comprising:
   a.) the balloon catheter of claim 1,
   b.) a dilator having a dilator lumen extending from a proximal end of the dilator to a distal end of the dilator, said dilator having a diameter closely fitting said balloon catheter lumen,
   c.) a microcatheter having a microcatheter lumen,
   d.) a guidewire slideable within a member selected from the group consisting of the dilator lumen and the microcatheter lumen, and
   e.) a clot retrieval device adapted to fit within the lumen of the balloon catheter with a retrieved clot.

38. The kit of claim 37 wherein the microcatheter is a balloon catheter.

39. The kit of claim 37 wherein the guidewire is adapted to slide within the dilator lumen.

40. The kit of claim 37 wherein the guidewire is adapted to slide within the microcatheter lumen.

41. A microballoon catheter kit comprising:
   a.) the balloon catheter of claim 1 of a flexibility, length, and diameter appropriate for a neurovascular microcatheter and having a microcatheter lumen,
   b.) a guidewire slideable within the microcatheter lumen, and
   c.) a clot retrieval device adapted to fit within the lumen of the balloon catheter and extend to a radially expanded state.

42. A method for removing an embolus from a vascular lumen, comprising the steps of:
   (a) introducing the balloon catheter of claim 1 to a position proximal said embolus,
   (b) extending a microcatheter from the distal end of said balloon catheter to penetrate the embolus,
   (c) extending a clot removal device through the embolus past the microcatheter,
   (d) inflating the balloon of said balloon catheter to temporarily occlude the vascular lumen,
   (e) withdrawing the microcatheter into the balloon catheter,
   (f) withdrawing the clot removal device and the embolus into the balloon catheter,
   (g) deflating the balloon of said balloon catheter, and
   (h) withdrawing the balloon catheter and embolus.

43. The method of claim 42 wherein the steps of withdrawing the microcatheter and withdrawing the clot removal device and the embolus into the balloon catheter are simultaneous.

44. The method of claim 42 wherein the microcatheter is a balloon microcatheter.

45. The method of claim 42 wherein the vascular lumen is the middle cerebral artery.

46. The method of claim 42 wherein the vascular lumen is in a human periphery or coronary.

47. A method for treating a site in a vascular lumen, comprising the steps of:
   (a) introducing the balloon catheter of claim 1 to a position in said lumen,
   (b) inflating the balloon of said balloon catheter to temporarily occlude the vascular lumen,
   (c) treating said site in the lumen,
   (d) deflating the balloon of said balloon catheter, and
   (e) withdrawing the balloon catheter.

48. The method of claim 47 wherein the microcatheter is a balloon microcatheter.

49. A method for performing a diagnostic step in a vascular lumen, comprising the steps of:
   (a) introducing the balloon catheter of claim 1 to a position in said lumen,
   (b) inflating the balloon of said balloon catheter to temporarily occlude the vascular lumen,
   (c) performing a diagnostic step at said site in the lumen,
   (d) deflating the balloon of said balloon catheter, and
   (e) withdrawing the balloon catheter.

50. The method of claim 48 wherein the microcatheter is a balloon microcatheter.

51. A microballoon catheter comprising:
   a first elongate polymeric tubular member having an outer surface, a proximal end, a distal end, a working lumen extending between said distal and proximal ends and being open at said distal end, and a radially recessed region near the distal end, and
   a longitudinally-stretched inflatable member situated within said radially recessed region providing a substantially constant diameter in a region adjacent and across the radially recessed region and being fluid-connectable with at least one fluid supply lumen independent of said working lumen wherein said catheter is of a flexibility, length, and diameter appropriate for a neurovascular microcatheter.

52. The microballoon catheter of claim 51, further comprising a second elongate polymeric tubular member substantially concentric with the first elongate tubular member and having a lumen forming the working lumen and an outer surface forming an annular space between the first elongate tubular member, said annular space being the fluid supply lumen.

53. The microballoon catheter of claim 52, wherein said second elongate tubular member comprises a wall, a distal end, and a proximal end, and further comprising a stainless steel braided stiffener member situated to provide kink resistance to the microballoon catheter.

54. The microballoon catheter of claim 53, wherein said first elongate tubular member is tapered distal of said inflatable member and joined to said second elongate tubular member.

55. The microballoon catheter of claim 54, wherein the first elongate tubular member comprises a polyether-polyamide block copolymer.

56. The microballoon catheter of claim 55, wherein said second elongate tubular member comprises a lubricious polymeric tubular inner-most tubing member.

57. The microballoon catheter of claim 56, wherein said lubricious polymeric tubular inner-most tubing member comprises polytetrafluoroethylene having a wall thickness of 0.25 to 1.5 mils.

58. The microballoon catheter of claim 57, wherein said second elongate tubular member further comprises a polyether-polyamide block copolymer outer-most tubing member.

59. The microballoon catheter of claim 58, wherein the second elongate member further comprises a radio-opaque marker band distal of said inflatable member.

60. The microballoon catheter of claim 59, wherein said substantially constant diameter is between one French (0.33 mm) and several millimeters.

61. A balloon catheter having a substantially constant diameter comprising:
- a first elongate tubular member having an outer surface, a proximal end, a distal end, a working lumen extending between said distal and proximal ends and being open at said distal end, and a radially recessed region near the distal end, and
- an inflatable member situated within said radially recessed region providing said substantially constant diameter and being fluid-connectable with at least one fluid supply lumen independent of said working lumen.

62. The balloon catheter of claim 61, further comprising a second elongate tubular member substantially concentric with the first elongate tubular member and having a lumen forming the working lumen and an outer surface forming an annular space between the first elongate tubular member, said annular space being the fluid supply lumen.

63. The balloon catheter of claim 62, wherein said second elongate tubular member comprises a wall, a distal end, and a proximal end, and further comprising a stiffener member situated to provide kink resistance to the balloon catheter.

64. The balloon catheter of claim 63, wherein the stiffener member comprises a braid.

65. The balloon catheter of claim 61, wherein the inflatable member is compliant.

66. The balloon catheter of claim 61, wherein said catheter is of a flexibility, length, and diameter appropriate for a neurovascular microcatheter.

67. The balloon catheter of claim 62, wherein the second elongate member further comprises a radio-opaque marker band distal of said inflatable member.

68. The balloon catheter of claim 62, wherein said first elongate tubular member is tapered distal of said inflatable member and joined to said second elongate tubular member.

69. The balloon catheter of claim 62, wherein said second elongate tubular member further comprises a lubricious polymeric tubular inner-most tubing member.

70. The balloon catheter of claim 61, wherein said first elongate tubular member comprises a polymeric tubing.

71. The balloon catheter of claim 61, wherein the inflatable member is longitudinally stretched upon attachment to the first elongate tubular member.

72. The balloon catheter of claim 71, wherein the inflatable member is stretched longitudinally at least 10% upon attachment to the first elongate tubular member.

73. The balloon catheter of claim 72, wherein the inflatable member is stretched longitudinally about 15% upon attachment to the first elongate tubular member.

* * * * *